United States Patent
Rabbett et al.

(10) Patent No.: US 6,948,352 B2
(45) Date of Patent: Sep. 27, 2005

(54) SELF-CALIBRATING CARBON MONOXIDE DETECTOR AND METHOD

(75) Inventors: Michael David Rabbett, Colorado Springs, CO (US); Ann Marie Harvey, Pangbourne (GB)

(73) Assignee: Walter Kidde Portable Equipment, Inc., Mebane, NC (US)

( * ) Notice: Subject to any disclaimer, the term of this patent is extended or adjusted under 35 U.S.C. 154(b) by 18 days.

(21) Appl. No.: 10/072,747

(22) Filed: Feb. 7, 2002

(65) Prior Publication Data

US 2003/0145644 A1 Aug. 7, 2003

(51) Int. Cl.[7] ............................................ G01N 27/407
(52) U.S. Cl. .................. 73/1.04; 73/1.03; 73/1.06; 73/23.31; 73/23.21; 204/401
(58) Field of Search ................... 73/1.04, 1.03, 73/1.06, 23.31, 23.21; 340/628, 632; 422/98, 83; 204/401

(56) References Cited

U.S. PATENT DOCUMENTS 6,200,443 B1 * 3/2001 Shen et al. .................. 204/401

FOREIGN PATENT DOCUMENTS

| EP | 0 611 112 A1 | 8/1994 | |
|---|---|---|---|
| EP | 0 744 620 A1 | 11/1996 | |
| EP | 0 890 837 A2 | 1/1999 | |
| GB | 2254696 A * | 10/1992 | .......... G01N/27/12 |
| GB | 2 291 189 A | 1/1996 | |
| GB | 2 356 708 A | 5/2001 | |
| SU | 1 781 324 | 12/1992 | |
| WO | WO 99/24826 | 5/1999 | |
| WO | WO 01/14864 A2 | 3/2001 | |

OTHER PUBLICATIONS

"The Electrochemistry of Gases: New Sensing Opportunities", by Emory S. De Castro, Jan. 1996 vol. 2 No. 1.

* cited by examiner

Primary Examiner—Hezron Williams
Assistant Examiner—Nashmiya Fayyaz
(74) Attorney, Agent, or Firm—Merchant & Gould P.C.

(57) ABSTRACT

The self-calibrating carbon monoxide detector and method of the present invention utilize the gas for which the detector was designed to detect as the calibration gas. Specifically, a carbon monoxide gas generator is included in the detector assembly, and is controller to produce a known amount of CO. The sensor response to the quantity of CO generated is monitored, and the calibration thereof adjusted as necessary. The operation of the gas generator is also monitored, and any failures are flagged for user attention. The gas generator specifically suppresses the generation of hydrogen through the materials used in its construction. Temperature effects may also be compensated either through control of gas generation control parameters or compensation of the sensor output in view of the generator temperature effects.

32 Claims, 7 Drawing Sheets

SELF-CALIBRATING CARBON MONOXIDE DETECTOR AND METHOD

FIELD OF THE INVENTION

The present invention relates generally to testing and calibration of hazardous condition detectors, and more particularly to self-contained, in-the-field calibration and testing of domestic carbon monoxide detectors.

BACKGROUND OF THE INVENTION

Public awareness of the dangers posed by carbon monoxide in the home and continuing advances in carbon monoxide detection technology and reliability has greatly increased the number of carbon monoxide detectors installed in homes. Unlike hazardous gas detectors for industrial applications that are serviced and calibrated regularly, carbon monoxide detectors for use in domestic applications are intended to be "fit and forget" devices. This places a major demand on the sensor used in a domestic gas detector as it must maintain its performance over periods that run into years, all without attention from the owner.

However, with the very long life times expected for a domestic carbon monoxide detector, possibly extending to five years or more, some degradation and loss of accuracy must be expected. Indeed, there are three main potential causes for loss of performance of the sensors typically used in domestic carbon monoxide detectors. First, the active part of the sensor, the membrane electrode assembly or "MEA," can be damaged by either loss of hydration or chemical poisoning. The effect of this is to reduce the output of the sensor for a particular level of carbon monoxide. As a result, the exposure times or concentration levels before an alarm will be sounded are increased. Second, the electrical contacts to the MEA can be lost. This results in a complete loss or intermittent output from the sensor in the presence of carbon monoxide, which results in no or intermittent alarm output in the presence of carbon monoxide. Third, the gas diffusion aperture in the top of the sensor could become blocked. This results in zero output from the sensor when carbon monoxide is in the environment because none of this carbon monoxide can reach the MEA. With each of these performance affecting events, the result is that the carbon monoxide alarm no longer provides adequate warning during periods of high carbon monoxide concentrations or long carbon monoxide exposures.

Recognizing the serious dangers posed by such a degradation in performance, some modern domestic carbon monoxide detectors employ a mechanism to apply hydrogen as a calibration gas to the top of the sensor. Indeed hydrogen is used as a calibration gas for all types of sensors that detect reducing gases, including carbon monoxide detectors. This is because electrochemical carbon monoxide sensors are capable of sensing a number of gases in addition to carbon monoxide. These gases include hydrogen, sulfur dioxide, and nitrogen oxides. Hydrogen is used as the calibration gas because it is easily produced, and is relatively non-toxic and safe, provided that the concentration is kept below explosive levels.

Unfortunately, while typical carbon monoxide sensors do react to hydrogen, the behavior of the sensor towards hydrogen is not the same as its behavior towards carbon monoxide. Specifically, under conditions of chemical poisoning of the MEA the sensitivity to hydrogen can actually increase while the sensitivity towards carbon monoxide decreases. In such a condition, utilization of hydrogen as the calibration gas will provide a false level of security that the carbon monoxide detector is operating properly when, in fact, its ability to sense carbon monoxide has been substantially impaired.

There exists, therefore, a need in the art for a domestic carbon monoxide sensor that provides reliable self calibration and testing of its ability to properly detect concentrations of carbon monoxide under various failure conditions, including poisoning of the MEA.

BRIEF SUMMARY OF THE INVENTION

In view of the above, it is a general aim of the present invention to provide a new and useful self-calibrating carbon monoxide detector.

In an embodiment of the present invention, a carbon monoxide detector comprises a housing forming a chamber and including an aperture, a carbon monoxide sensor assembly having an aperture positioned within the chamber, and a carbon monoxide gas generator assembly also having an aperture positioned within the chamber. The detector further comprises a controller coupled to the carbon monoxide sensor assembly and to the carbon monoxide gas generator assembly. This controller commands the carbon monoxide gas generator assembly to produce carbon monoxide, and monitors the electrical output of the carbon monoxide sensor assembly to ensure its proper operation.

In a further embodiment of the present invention, a carbon monoxide sensor assembly comprises a can forming a water reservoir and a bottom disk positioned within the can to separate the water reservoir from an upper sensor portion of the can. This bottom disk includes at least one aperture. A hydrophobic layer is positioned on the bottom disk and covers the aperture of the bottom disk. An electrode assembly is positioned on the hydrophobic layer, and a first washer positioned on that electrode assembly. This first washer has an outer periphery that is closely accommodated by the inner surface of the can, defines a hole having a diameter that is smaller than a diameter of the electrode assembly. A diffusion layer is positioned on this first washer, and a second washer is positioned on the diffusion layer. This second washer also has an outer periphery that is closely accommodated by the inner surface of the can, and defines a hole having a diameter that is smaller than the diameter of the diffusion layer. A gasket is positioned on this second washer, and a top disk is positioned in sealing engagement with the gasket. This top disk includes an aperture. In a preferred embodiment the can is crimped to seal the carbon monoxide sensor assembly. The diffusion layer is deformed within the assembly to provide electrical contact between the top disk and a top of the electrode assembly. The electrical contact between a bottom of the electrode assembly and the can is provided by the hydrophobic layer and the bottom disk.

In an additional embodiment of the present invention, a carbon monoxide gas generator assembly comprises a can forming a water reservoir, and a bottom disk positioned within the can to separate the water reservoir from an upper generator portion of the can. This bottom disk includes at least one aperture. A hydrophobic layer is positioned on the bottom disk covering the aperture, and an electrode assembly is positioned on the hydrophobic layer. This electrode assembly comprises an ion exchange membrane having electrodes deposited on an upper and on a lower surface. The electrodes contain a mixture of carbon black and ion exchange polymer and no platinum. A diffusion layer is provided, as is a gasket. A top disk in sealing engagement with the gasket is also provided and includes an aperture.

Preferably, the can is crimped to seal the carbon monoxide gas generator assembly. The diffusion layer provides electrical contact between the top disk and a top of the electrode assembly. The electrical contact between a bottom of the electrode assembly and the can is provided by the hydrophobic layer and the bottom disk.

In an alternative embodiment of the present invention, a carbon monoxide gas generator assembly comprises a can forming a water reservoir and a bottom disk positioned within the can to separate the water reservoir from an upper generator portion of the can. The bottom disk includes at least one aperture. A hydrophobic layer containing no platinum is positioned on the bottom disk covering the aperture. An electrode assembly is positioned on the hydrophobic layer. This electrode assembly comprises an ion exchange membrane. A diffusion layer containing no platinum is positioned to contact the electrode assembly. A gasket is provided, and a top disk in sealing engagement with the gasket is also provided. The top disk defines an aperture. Preferably, the can is crimped to seal the carbon monoxide gas generator assembly. The diffusion layer provides electrical contact between the top disk and a top of the electrode assembly, and electrical contact between a bottom of the electrode assembly and the can is provided by the hydrophobic layer and the bottom disk.

In a further alternate embodiment of the present invention, a method of calibrating a carbon monoxide detector having a carbon monoxide sensor and a carbon monoxide gas generator in gaseous communication comprises the steps of controlling the carbon monoxide gas generator to generate a known quantity of carbon monoxide, monitoring a response of the carbon monoxide sensor to the known quantity of carbon monoxide, and correcting a calibration of the carbon monoxide sensor when the response is outside of a predetermined range.

Other objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

The system and method of the present invention, as will be discussed below, provides reliable, automatic testing of a carbon monoxide detector and allows calibration of the detector based on the results of the test. This functionality is provided by the generation of a small amount of the gas for which the detector is designed to detect. For a carbon monoxide detector, the test and calibration gas generated is carbon monoxide.

Unlike the system of the present invention, when using a platinum electrode on the MEA to electrolyze water as is typical in most self-calibrating detectors, the gas evolved at the positive terminal of the electrode is usually oxygen, while the gas evolved at the negative terminal is usually hydrogen. However, as discussed above, using hydrogen as the calibration gas does not properly detect chemical poisoning of the MEA. In fact, under such conditions the sensor response to hydrogen gas increases while the response to carbon monoxide actually decreases. In such cases, the sensor will erroneously be determined to be functioning properly.

In the self-calibrating carbon monoxide detector of the present invention, hydrogen gas is specifically not used as the calibration gas. In fact, the production of hydrogen is specifically suppressed. The negative electrode is modified by an electrochemical oxidation treatment to form a surface covering of carbon-hydrogen-oxygen complexes, and this covering is rapidly replenished if it is removed, so that hydrogen production is suppressed and the reduction of oxygen is promoted. Through experimentation it was discovered that when using carbon electrodes, instead of platinum, the oxygen ions produced by electrolysis of water within the electrolyte are not discharged as molecular oxygen at the positive electrode, but react with the electrode surface to produce CO and $CO_2$. Typically 5% of the gases produced will be in the form of CO and 95% will be $CO_2$ (note the sensor does not respond to $CO_2$). Thus the use of carbon electrodes in the present invention has two purposes, to wit, to promote the production of carbon monoxide at the positive terminal and suppress the production of hydrogen at the negative terminal.

The production of CO by electrolysis of dilute sulphuric acid solution using carbon electrodes is known in the scientific literature. However, the gas generator of the present invention is based on the production of carbon monoxide by electrochemical processes using an ion transporting membrane (also know as an ion exchange membrane) to act as the electrolyte. In a preferred embodiment of the present invention a product known as Nafion produced by DuPont is used. An ion transporting membrane such as Nafion behaves in a manner that is very similar to the acid solution process just mentioned, except that it is a solid rather than liquid. Nafion and other similar materials are capable of supporting the transport of protons between the two electrodes of an electrochemical cell in the same way that sulphuric acid does. However, in order to function efficiently the Nafion membrane must be kept supplied with water vapor from an attached water reservoir. When it is correctly hydrated, the passage of a few milliamperes of current at a voltage of typically 3 V and with a duration of a few seconds, can produce a CO gas concentration of approximately 100 ppm.

In practice, the noise and drift of a real carbon monoxide sensor amount to a few ppm equivalent. In addition, the Underwriters Laboratory (UL) standard for domestic carbon monoxide detectors (UL2034) specifies that these detectors should neither display a CO concentration of less than 30 ppm or alarm at less than 30 ppm. Therefore, if the concentration of the calibration gas transferred from the gas generator to the sensor is kept below 30 ppm it will not be necessary to blank the display of the detector during a self-calibration event. Further, at such low concentrations there will be no possibility of the detector sounding an alarm during the self-calibration process, and therefore no need to artificially silence the alarm.

In one embodiment of the self-calibrating detector of the present invention, the physical construction of the carbon monoxide sensor and the gas generator are similar, differing primarily in the materials for the individual parts. Therefore, to simplify the discussion of these two components reference to FIGS. 1 and 2 will be used to describe both the detector and the gas generator. However, when differences in material are important in the construction of a particular element of each of these components, such differences will be discussed with relation to the particular element and its reference numeral.

Figure 1:
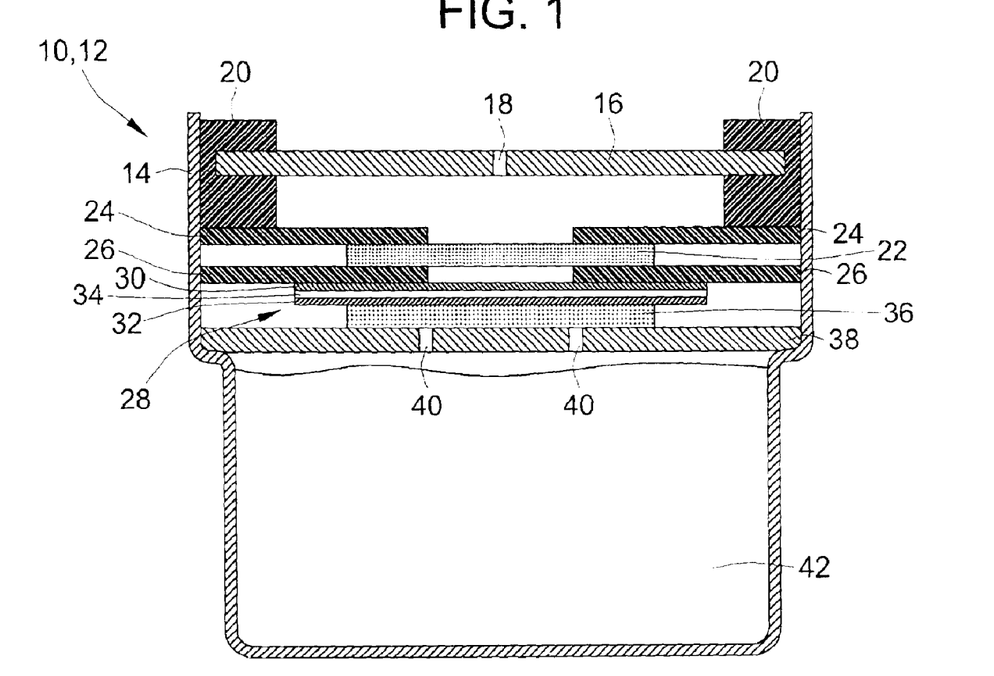
FIG. 1 is a simplified assembly diagram of a carbon monoxide gas sensor and/or generator constructed in accordance with one embodiment of the present invention prior to crimping.
Figure 2:
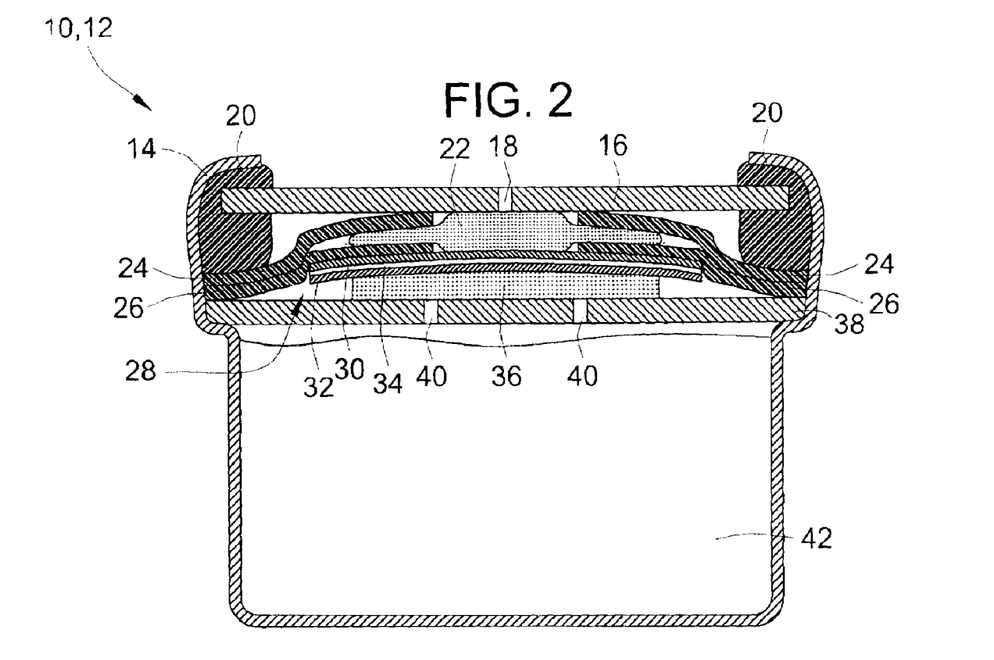
FIG. 2 is a simplified assembly diagram of the carbon monoxide gas sensor and/or generator of FIG. 1 after crimping.

With reference to FIG. 1, the individual components of a carbon monoxide sensor 10 or a carbon monoxide gas generator 12 are illustrated in a state before the can 14 is crimped closed. FIG. 2 illustrates these same components after crimping. The crimping process compresses the internal parts to ensure good water tight sealing and good electrical contact within the sensor. The individual components that form the sensor 10 or gas generator 12 are arranged in a stack and comprise a top disk 16, a gasket 20, a diffusion layer 22, two plastic washers 24, 26 (may not be present in a carbon monoxide gas generator 12), an electrode assembly 28, a hydrophobic layer 36, and a bottom disk 38. Below this stack is a water reservoir 42.

In a preferred embodiment of the present invention, the top disk 16 is made from a rigid stainless steel disk, and is used to apply compression to the other components. The disk 16 has an aperture 18 in the center to allow access for carbon monoxide to the active parts of the sensor 10 (in the case of a sensor assembly 10), or to allow carbon monoxide produced in the active parts of the gas generator 12 to escape the can 14 to test the sensor 10. In embodiments of the sensor 10 and generator 12, the aperture 18 controls the rate at which CO can diffuse into the sensor 10 or out of the gas generator 12. However, in other embodiments this aperture 18 is not diffusion limiting as will be discussed below.

The gasket 20 is preferably a silicon rubber gasket or other appropriate material that is capable of sealing the crimped assembly 10, 12 against loss of water. The seal provided by the gasket 20 also ensures that the only means of carbon monoxide entry into or out of the assembly 10, 12 is through the aperture 18 in the top disk 16. In this way the readings from the sensor 28 during normal operation and testing, and the amount of gas produced for calibration are known and relate to a particular concentration of carbon monoxide based on the diffusion rate through the aperture 18.

The diffusion layer 22 has two functions. First, it provides electrical contact between the top disk 16 and the upper surface of the electrode assembly 28. Second, it allows carbon monoxide that enters the sensor 10 to diffuse sideways and react with substantially the whole are of the electrode assembly 28. When the sensor 10 has been crimped closed as illustrated in FIG. 2, this diffusion layer 22 undergoes significant distortion. This ensures good electrical contact between the top disk 16 and the upper surface of the electrode assembly 28. The material for this diffusion layer 22 must be porous to gases and electrically conductive. In one embodiment a microporous carbon loaded PTFE compound such as Carbel (produced by W L Gore) is used, although other carbon loaded materials may also be used.

The two components 24, 26 are identical and comprise two thin plastic washers with a hole diameter that is smaller than the diameter of diffusion layer 22 and an outer diameter that is just less than the inside diameter of the throat of the uncrimped can 14. The material of these washers 24, 26 can be PTFE or Polyethylene in a variety of grades. The purpose of the washers 24, 26 is twofold. First, the upper washer 24 is placed so as to prevent any organic vapors that can pass through the gasket 20 from reaching the electrode assembly 28. Second, the placement of the lower washer 26 is arranged to control the diffusion of carbon monoxide from the upper surface of the electrode assembly 28 to the lower surface of the electrode assembly 28. When the sensor 10 is crimped closed, the washers 24, 26 are forced against the bottom disk 38 and provide a seal at that point. In addition the top washer 24 is forced against the top disk 16 and provides a seal at that point.

The electrode assembly 28 is the working part of the sensor 10. In one embodiment the assembly 28 comprises an ion exchange membrane 34 (such as, e.g., Nafion 115 produced by DuPont) that is coated with an upper 30 and a lower 32 electrode. The construction and function of these electrodes in a carbon monoxide detector is described in U.S. Pat. No. 6,200,443, entitled GAS SENSOR WITH A DIAGNOSTIC DEVICE, issued Mar. 13, 2001, and assigned to Atwood Industries, Inc., the teachings and disclosure of which are hereby incorporated in their entireties by reference thereto. In order to work correctly, the assembly 28 must be kept humidified by water vapor from the water reservoir 42.

The hydrophobic layer 36 is made from the same material as the diffusion layer 22 and is designed to provide the electrical contact between the bottom disk and the lower surface 32 of the assembly 28. It has a further function, that of preventing the access of liquid water from the reservoir 42 to the electrode assembly 28. Thus the material for the diffusion layer 22 and the hydrophobic layer 36 must also possess hydrophobic properties. Note also that the presence of the hydrophobic layer 36 assists in causing the upward distortion of the electrode assembly 28, which helps in providing electrical contact to the upper surface 30 of the assembly 28.

A stainless steel bottom disk 38 is also included in the detector assembly 10. This disk 38 is strong enough to support the compression of the stack of components after the sensor can 14 is crimped closed. The disk 38 also contains one or more apertures 40 designed to allow the passage of water vapor from the reservoir 42 to the electrode assembly 28.

As stated earlier, the construction of a carbon monoxide sensor 10 and a calibration gas generator 12 are substantially the same, except that in one embodiment some of the components may be omitted and in other embodiments some parts are made of different materials. In the embodiment of the calibration gas generator 12 illustrated in FIGS. 1 and 2, the electrode assembly 28 may be a composite structure of ion exchange membrane 34 with deposited electrodes 30, 32. In this embodiment of the calibration gas generator 12, the electrodes 30 and 32 contain only a mixture of carbon black and ion exchange polymer. They contain no platinum, as is the case with the electrodes 30, 32 of the sensor 10, because the generation of hydrogen is to be suppressed and the generation of carbon monoxide is to be promoted.

As was discussed above, when using carbon electrodes 30, 32 in the calibration gas generator 12, instead of platinum electrodes in the carbon monoxide sensor 10 construction, the negative electrode is modified by an electrochemical oxidation treatment to form a surface covering of carbon-hydrogen-oxygen complexes, and this covering is rapidly replenished if it is removed. The oxygen ions that are involved in the electrolysis react with the electrode surface to produce CO and $CO_2$. The other electrode reaction, that at the negative electrode, is also modified and species like methane and ethylene are evolved instead of hydrogen. Thus the use of carbon electrodes in the calibration gas generator 12 of the present invention promotes the production of carbon monoxide at the positive terminal and suppresses the production of hydrogen at the negative terminal.

Figure 3:
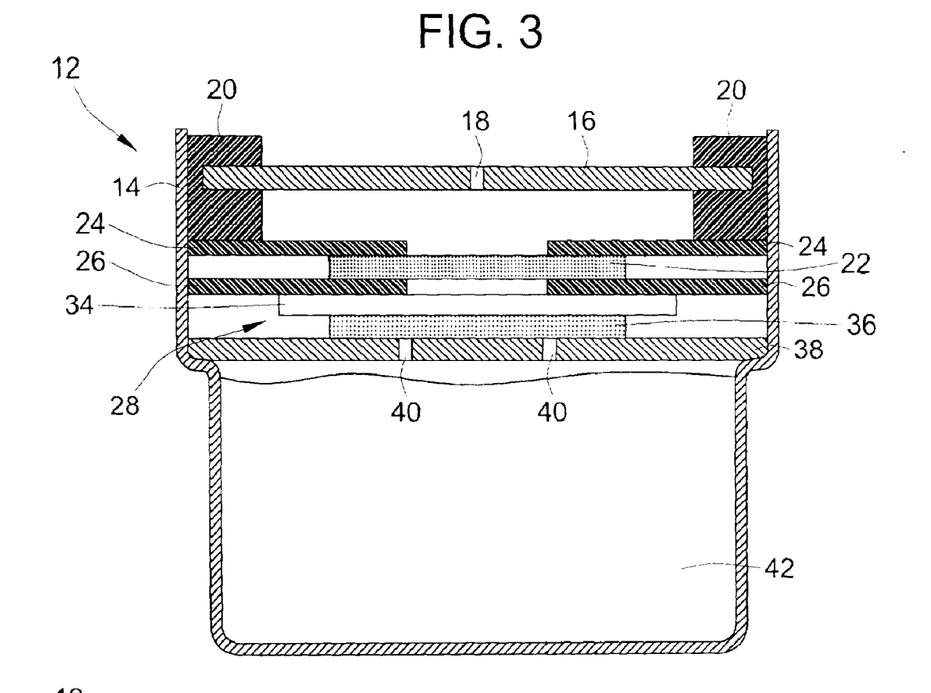
FIG. 3 is a simplified assembly diagram of a carbon monoxide gas generator constructed in accordance with an embodiment of the present invention prior to crimping.
Figure 4:
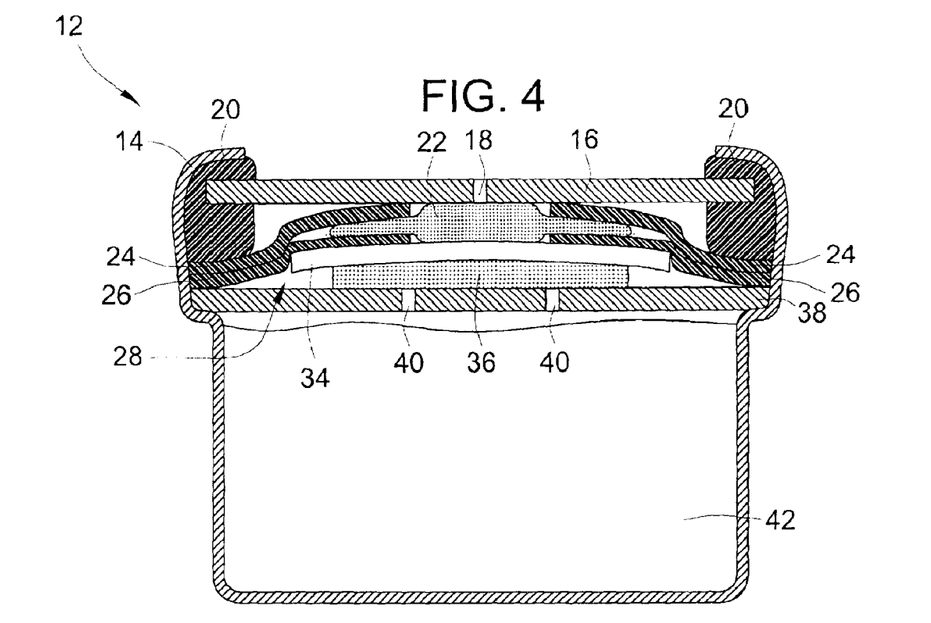
FIG. 4 is a simplified assembly diagram of the carbon monoxide gas generator of FIG. 3 after crimping.

In the embodiment of the calibration gas generator 12 illustrated in FIGS. 3 and 4, the assembly 28 may include just the ion exchange membrane 34. In this embodiment of the calibration gas generator 12, the assembly 28 consists simply of a sheet of ion exchange membrane 34. The electrodes are provided by the diffusion layer 22 and the hydrophobic layer 36. These layers 22, 34, as discussed above, are made of a carbon containing gas porous material. As such, they satisfy the requirement of hydrogen suppression and carbon monoxide generation.

Figure 5:
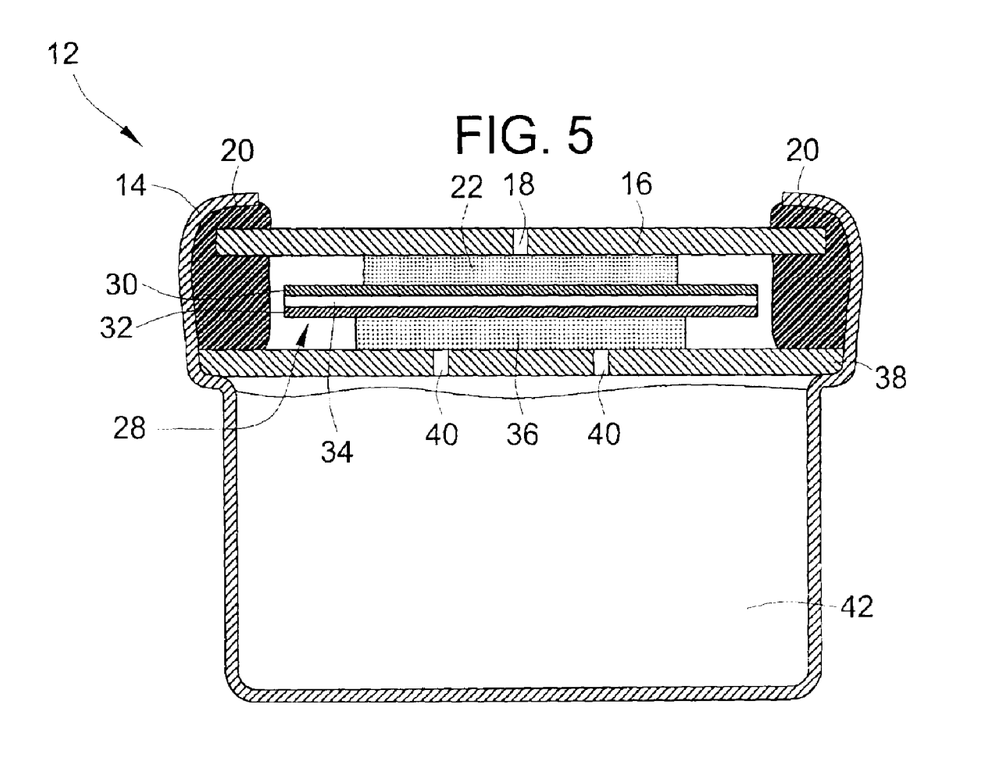
FIG. 5 is a simplified assembly diagram of a carbon monoxide gas generator constructed in accordance with another embodiment of the present invention after crimping.

Unlike a carbon monoxide sensor 10, the requirement for resistance to chemical poisoning is not present for a carbon monoxide gas generator 12. As such, the washer 24 may or may not be used. Likewise, the requirement to control the diffusion of gases around the assembly 28 is less important in a gas generator 12 than in a gas sensor 10, and so the washer 26 may or may not be used. FIG. 5 illustrates an embodiment of the gas generator 12 of the present invention that does not include these washers. While this embodiment illustrates the use of electrodes 30, 32 in the assembly 28, layers 22 and 36 could serve this function as discussed above. In such an embodiment, only the ion exchange membrane 34 would be needed in the assembly 28 similar to that illustrated in FIGS. 3 and 4.

Having now discussed the construction of both the carbon monoxide gas detector 10 and the carbon monoxide gas generator 12, attention is now focused on the construction of a self-testing and/or a self-calibrating carbon monoxide sensor 44. For simplicity of disclosure, the following will discuss a self-calibrating carbon monoxide sensor 44 that includes both testing and calibration functions. Such a sensor 44 is comprised of a carbon monoxide sensor 10, a carbon monoxide gas generator 12, and a housing 46 to connect the two main components 10, 12 together. The sensor 44 also includes appropriate driver/detection electronics, a calibration algorithm and a control program. Each of these will be discussed in turn below.

Figures 6, 7, 8, 9, 10:
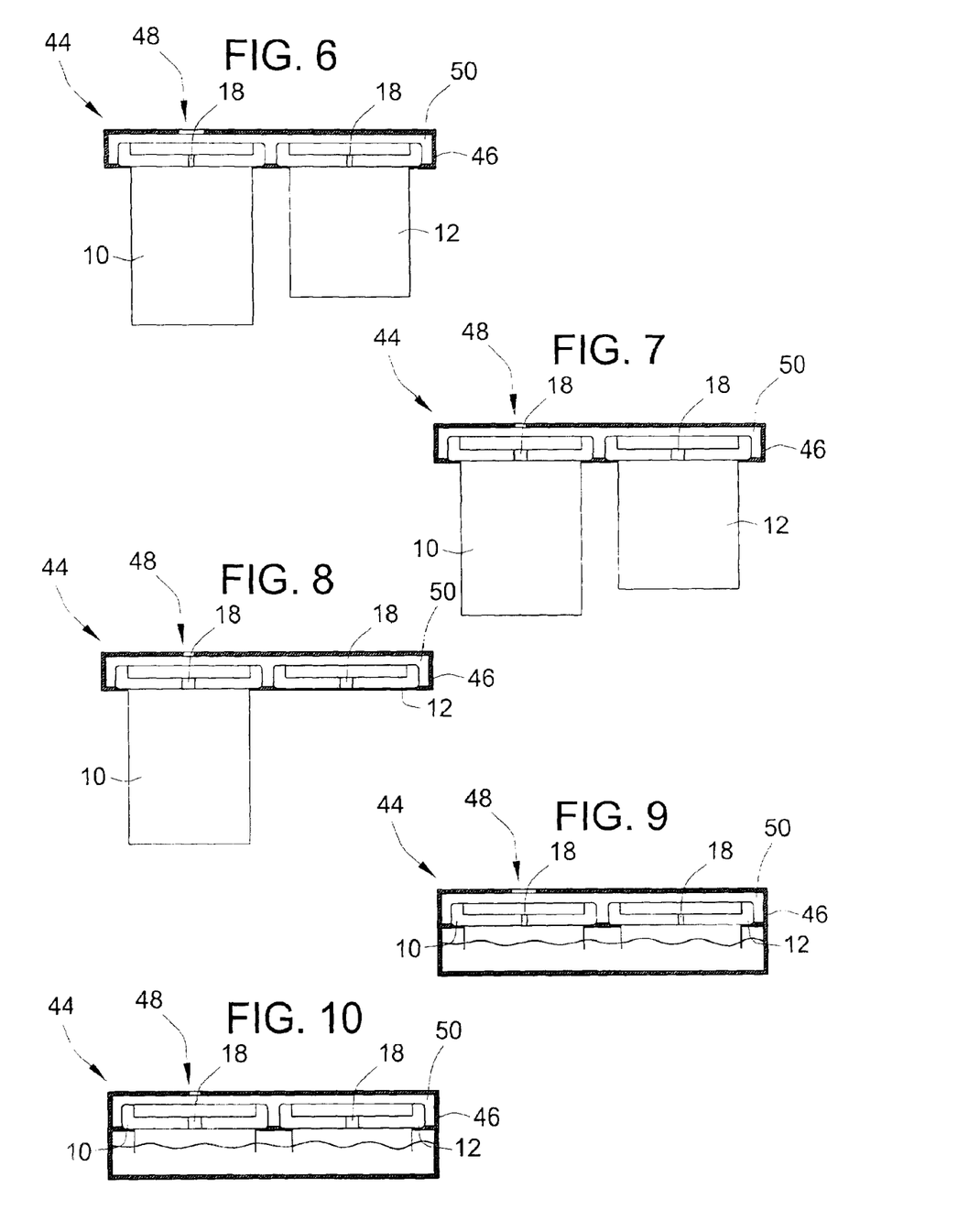
FIG. 6 is a schematic diagram illustrating a self calibrating carbon monoxide detector constructed in accordance with an embodiment of the present invention.
FIG. 7 is a schematic diagram illustrating a self calibrating carbon monoxide detector constructed in accordance with an alternate embodiment of the present invention.
FIG. 8 is a schematic diagram illustrating a self calibrating carbon monoxide detector constructed in accordance with a further embodiment of the present invention.
FIG. 9 is a schematic diagram illustrating a self calibrating carbon monoxide detector constructed in accordance with yet another embodiment of the present invention.
FIG. 10 is a schematic diagram illustrating a self calibrating carbon monoxide detector constructed in accordance with an additional embodiment of the present invention.

With reference to FIGS. 6–10, the connection of the sensor 10 and generator 12 together through the housing 46 is discussed. The electrical connections have been omitted for clarity. In the various embodiments of the sensor 44 illustrated in these figures, the location of the diffusion-controlling aperture is one of the distinguishing features between these embodiments. In the embodiment of FIG. 6, sizing the aperture 18 of the top disk of each component 10, 12 to be the diffusion-controlling apertures of the sensor 44 reduces the need for sealing of the electrical connections to the two components 10, 12 where they pass through the wall of the coupling chamber housing 46. However, this does increase the response time for calibration and decreases the peak signal. These apertures 18 control the entry (for sensor 10) and exit (for generator 12) of carbon monoxide and water vapor into the sensor 44. Thus the apertures 18 control the sensitivity of the sensor 10, the rate of release of calibration gas from the generator 12, and the rate of water loss from both parts 10, 12.

The generator 12 and sensor 10 are coupled by a small chamber 50 formed by housing 46. The chamber 50 should be arranged to have a small volume. Minimization of the volume of this chamber 50 minimizes the quantity of calibration gas that must be produced, and improves the speed of response of the system. A secondary non-diffusion limiting aperture 48 is present in the wall 46 of the connecting chamber 50 in order to allow carbon monoxide to enter the sensor 44 from the ambient environment. The sensor 10 and generator 12 can be oriented side-by-side as shown, or end-to-end with the two top disks placed in close proximity. In this embodiment, both the sensor 10 and generator 12 must have their own water reservoirs.

In another embodiment of the self-calibrating sensor 44 illustrated in FIG. 7, the separate generator 12 and sensor 10 each have a larger, non-diffusion limiting aperture 18 in their top caps. These larger apertures 18 do not limit the diffusion rate of carbon monoxide and water vapor into or out of the sensor 10 and generator 12, respectively. The two components 10, 12 are then connected by a small chamber 50 that is fitted with a diffusion-controlling aperture 48 as shown. This allows free communication of both calibration gas and water vapor between the sensor 10 and generator 12 and leads to a faster and larger response of the sensor to the calibration event. The free movement of water vapor between the sensor 10 and generator 12 means that only a single water reservoir may be necessary as is illustrated in the embodiment of FIG. 8. Indeed, this free movement allows the water reservoir to be included with either the sensor 10 (as shown) or the generator 12 (not shown). Alternatively, both components 10, 12 can be equipped with smaller water reservoirs than those required in FIGS. 6 and 7.

In yet a further embodiment of the present invention, the sensor 10 and generator 12 share a common water reservoir as shown in FIGS. 9 and 10. This may be achieved by removing the bottom part of the can of both the sensor and generator and immersing the open ends into a common water reservoir. One advantage of this is that the overall dimensions of the self-calibrating sensor 44 may be smaller than that of the previous embodiments for the same volume of water. The sensor 10 and generator 12 may be equipped with their own individual diffusion controlling apertures 18 as illustrated in the embodiment of FIG. 9, in which case the aperture 48 is non-diffusion controlling. Alternatively, the aperture 48 in the wall of the communicating chamber 50 can be sized to be diffusion controlling and the apertures 18 in the sensor 10 and the generator 12 can be non-diffusion controlling as shown in FIG. 10.

Having now discussed the construction of the individual components 10, 12 and the construction of the self-calibrating carbon monoxide assembly 44, attention is now turned to the method of testing and self-calibration of the present invention. The testing and self-calibration process comprises basically applying an electrical pulse to the gas generator 12 and then observing the effect on the output of the sensor 10. However, the practical implementation of this method is more complicated as will be discussed below.

In an electrochemical gas generator where there are no unwanted side reactions competing with the desired electrochemical reaction, the amount of gas produced is directly proportional to the number of electrons that pass through the generator. The number of electrons is determined by the time integral of the current that passes through the generator. Therefore controlling the volume of gas produced with each electrical pulse can best be achieved by controlling both the pulse current and the duration of the pulse. Thus the drive circuit for the gas generator preferably includes a constant current source. Such a current source delivers a preset current irrespective of the voltage required. To control the current pulse duration, a timing process control element is included with the current source. In accordance with an embodiment of the present invention, the CO generator 12 requires typically <10 mA of current applied for a few seconds.

The polarity of the electrical pulse applied to the generator is important. In order for the generator to produce carbon monoxide by the electrochemical process described earlier, it is necessary that the electrode 30 (22 in the embodiments of FIGS. 3 and 4) that is nearest to the exit aperture 18 of the generator 12 be made positive with respect to the other electrode 32 (36 in the embodiments of FIGS. 3 and 4). If the polarity is reversed it is likely that the gas that enters the sensor 10 during calibration will not be predominantly carbon monoxide.

It is envisioned that the production of carbon monoxide may be temperature dependent in at least some embodiments or installations of the present invention. The reason for this is that electrochemical processes have reaction rates that show an exponential dependence on temperature. To deal with such temperature dependence, one embodiment of the present invention varies the magnitude of the applied current as a function of the ambient temperature. In another embodiment the applied pulse duration is varied as a function of the ambient temperature. In each of these embodiments, the variation based on ambient temperature is accomplished so that the amount of carbon monoxide produced by the generator 12 is a known quantity. While the production of carbon monoxide in the generator 12 may be temperature dependent, the ambient temperature has very little effect on the sensor 10 over the range of temperatures where a domestic detector 44 would be expected to operate. Therefore, temperature compensation of the sensor response may not be required.

In another embodiment of the present invention, the sensor reading is compensated or adjusted to take into account the temperature dependence of the production of the carbon monoxide by the generator 12. In this embodiment the ambient temperature is measured and the sensor response is corrected appropriately using a stored mathematical algorithm. This algorithm compensates for the increased or decreased amount of carbon monoxide that is produced by the generator 12 at the given ambient temperature.

In a further embodiment of the present invention, the output of the sensor is corrected automatically using a temperature sensitive load resistor network. Alternatively, a temperature sensitive amplifier may be used to adjust the output of the sensor based on the ambient temperature. However, it is again stated that the compensation of the output of the sensor is performed, not because the sensor is adversely affected by the ambient temperature, but because the generator 12 produces a different quantity of carbon monoxide at different temperatures, unless its driving circuitry is compensated as discussed above.

As a further alternate embodiment, the system of the present invention ensures that the ambient temperature is within a limited allowable range before enabling a calibration event. In this way, the amount of carbon monoxide produced will be within a known limited range. As such the response of the sensor 10 can reliably be measured and compensated.

Additionally, before the calibration event is initiated it is necessary to measure the sensor signal 58 to determine the value of $S_{back}$. In a normal ambient environment $S_{back}$ should have a value of less than 5 ppm. However, under some abnormal atmospheric conditions, or if the sensor has been exposed to a large concentration of certain organic contaminants, the value of $S_{back}$ can be higher. However, under these conditions it should still be possible to perform a good calibration so long as the value of $S_{back}$ is stable. This can be checked by measuring the rate of change of $S_{back}$ over a short period of time. It is only when the value of $S_{back}$ exceeds the UL alarm threshold of 30 ppm that the calibration event will need to be aborted. This is because there is a possibility that the detector may be approaching an alarm condition. If the value of $S_{back}$ is acceptable (i.e. 5 ppm or less, or less than 30 ppm and stable), then the value of $S_{back}$ can be subtracted from either speak or the average value measured during the integration period ($t_{start}$ to $t_{stop}$). This is possible because, at low background levels, the sensor signals are simply additive. As such, the background can he removed by the simple subtraction of this level. The voltage developed across a correctly operating generator is shown in FIG. 11, along with the types of voltage waveforms produced by faulty generators.

Figure 11:
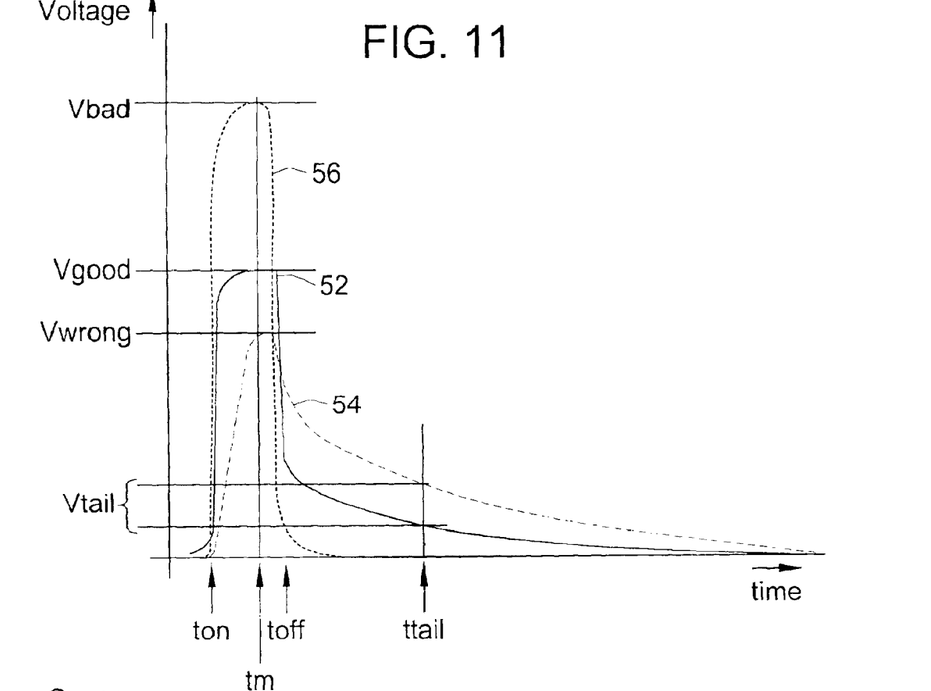
FIG. 11 is a graphic illustration of a voltage developed across the carbon monoxide generator to ensure proper operation thereof.

In this FIG. 11, the current drive to the generator 12 is switched on at time $t_{on}$ and switched off at time $t_{off}$. Voltage measurements are made at times $t_m$ and $t_{tail}$. In a practical system the time delay between $t_{on}$ and $t_{off}$ is typically 10 seconds and $t_m$ will occur approximately ¾ of the way through the pulse (e.g. at typically 7.5 seconds after $t_{on}$). The time $t_{tail}$ is typically 30 seconds to 1 minute after $t_{on}$. The voltage of waveform 52 measured at time $t_m$ is representative of the primary electrochemical reaction occurring in the gas generator 12, which would normally have a value $V_{good}$, where $V_{good}$ is in the range 2.9 V to 4 V. A generator that is not fully initialized and likely to be producing only low concentrations of CO would produce a voltage waveform 54 having a value of $V_{wrong}$, where $V_{wrong}$ will be less than 2.3 V. A generator producing a voltage waveform 56 having a value of $V_{bad}$ is representative of a carbon monoxide generator at the end of its useful life ($V_{bad}$ will be 4.5 V or higher). The voltage measured at time $t_{tail}$ is referred to as $V_{tail}$ and would be less than 0.1 V for a good generator.

Figure 12:
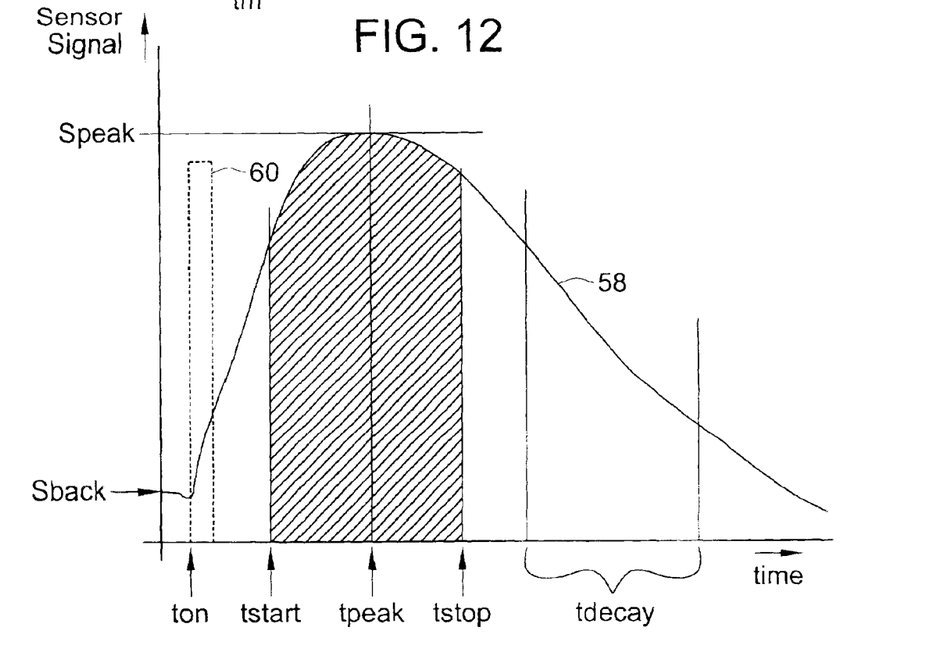
FIG. 12 is a graphic illustration of the behavior of the carbon monoxide sensor in response to operation of the carbon monoxide generator of the present invention.

The behavior of the sensor 10 in response to the amount of carbon monoxide produced as a result of the current applied to the gas generator 12 will typically be as shown as waveform 58 in FIG. 12. Immediately before the current is applied to the generator 12 at $t_{on}$ (represented as waveform 60), the waveform 58 will have a level of $S_{back}$. A second or two after $t_{on}$ the signal 58 from the sensor 10 will start to rise, and it will reach a peak $S_{peak}$ at time $t_{peak}$, before decayong back towards zero.

The behavior of the sensor signal 58 between $t_{on}$ and $t_{peak}$, and the delay between $t_{on}$ and $t_{peak}$, will be determined by the sizes of the apertures 18 (see FIGS. 6–10) in both the gas generator 12 and the sensor 10. The larger these apertures 18, the faster the gas will travel from the generator 12 to the sensor 10 and hence the shorter the delay. The volume of the connecting chamber 50 (see FIGS. 6–10) also has an effect on the waveform 58. That is, a larger volume will delay $t_{peak}$ and will reduce $S_{peak}$. This points out the need to minimize the chamber 50 volume. Likewise, the behavior of the sensor signal 58 during the period indicated as $t_{decay}$ is controlled by the chamber 50 volume. The behavior may also be affected by the catalytic power of the electrodes in the sensor 10 if the apertures 18 are non-diffusion limiting, or by the effective size of the aperture 48 from the chamber 50 to the ambient environment if the aperture 48 is non-diffusion limiting.

There are two features of the sensor signal 58 that may be used to define the output of the calibration event, the value of $S_{peak}$ and the integrated value of the sensor signal between $t_{start}$ and $t_{stop}$ (the shaded area in FIG. 12). The start time $t_{start}$ will typically be about 10 seconds before $t_{peak}$ and the stop time $t_{stop}$ will be about 10 seconds after $t_{peak}$. These times will normally remain fixed for the life of the gas generator 12.

Additionally, before the calibration event is initiated it is necessary to measure the sensor signal 58 to determine the value of $S_{back}$. In a normal ambient environment $S_{back}$ should have a value that is equivalent to a carbon monoxide concentration of less than 5 ppm. If the value Of $S_{back}$ is equivalent to a concentration of more than 5 ppm of CO, and especially if it is above 30 ppm of CO, the calibration event will need to be aborted. This is because there is a possibility that the detector may be approaching an alarm condition. If the value of $S_{back}$ is acceptable (i.e. 5 ppm or less), then the value of $S_{back}$ can be subtracted from either $S_{peak}$ or the average value measured during the integration period ($t_{start}$ to $t_{stop}$). This is possible because, at low background levels, the sensor signals are simply additive. As such, the background can be removed by the simple subtraction of this level.

Figure 13:
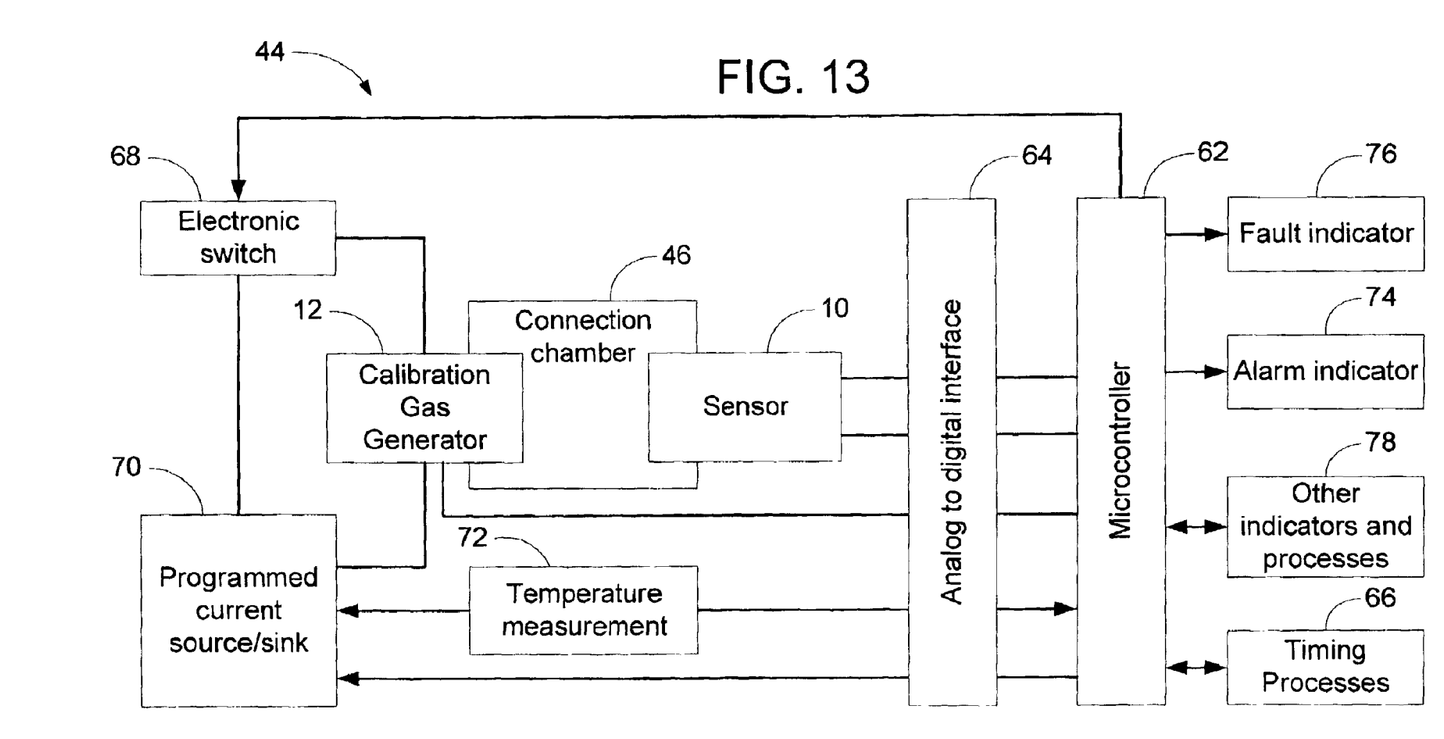
FIG. 13 is a simplified control block diagram of an embodiment of a self calibrating carbon monoxide detector constructed in accordance with the teachings of the present invention.

In one embodiment of the present invention, the detector assembly 44 will contain a programmed microcontroller 62 or other logic device (e.g. PLA, ASIC, etc.) as illustrated in FIG. 13. The microcontroller 62 is designed to operate the detector 44 and provide all the normal functionality of a carbon monoxide detector, calculate the time to initiate a calibration event, control the calibration event and initiate any calibration changes or other events that the result of the calibration event requires. The microcontroller 62 interfaces with the components of the detector 44 through analog/digital conversion circuitry 64. This circuitry 64 may be internal to the microcontroller 62. The microcontroller 62 also interfaces with timing process circuitry 66 to effectuate the carbon monoxide alarming functions and the testing and calibration functions as discussed above. The microcontroller 62 utilizes the alarm indicator circuitry 74 upon sensing a carbon monoxide alarm condition to warn occupants of the condition. The fault indicator circuitry 76 is utilized by the microcontroller 62 upon sensing a fault in the detector 44. An interface to other indicators and processes 78 may also be provided.

The generation of the calibration gas is controlled in one embodiment through the use of an electronic switch 68 to apply a current pulse from a programmed current source/sink 70 to the calibration gas generator 12 as discussed above. During the testing/calibration event the voltage of the generator 12 may be monitored to detect the operational status of the generator 12. If a fault is detected, the microprocessor may signal the occupant through the fault indicator circuitry 76. It is noted that the current pulse is controlled such that the amount of carbon monoxide gas generated is below the display and alarm concentrations. In this way, there is no chance that the detector 44 will display or alarm during the test/calibration event. Of course, a test/calibration indicator may be provided as part of the other indicators 78 provided with the detector assembly 44 as desired.

Also as discussed above, temperature compensation may be accomplished through the provision of temperature measurement circuitry 72. This temperature measurement circuitry 72 may provide an input to the programmed current source/sink circuitry 70 in embodiments that compensate the generator 12 performance for temperature described above. Temperature information may also be provided to the microcontroller 62 to allow compensation of the sensor 10 output due to temperature variations of the generator 12, also as discussed above.

Figure 14:
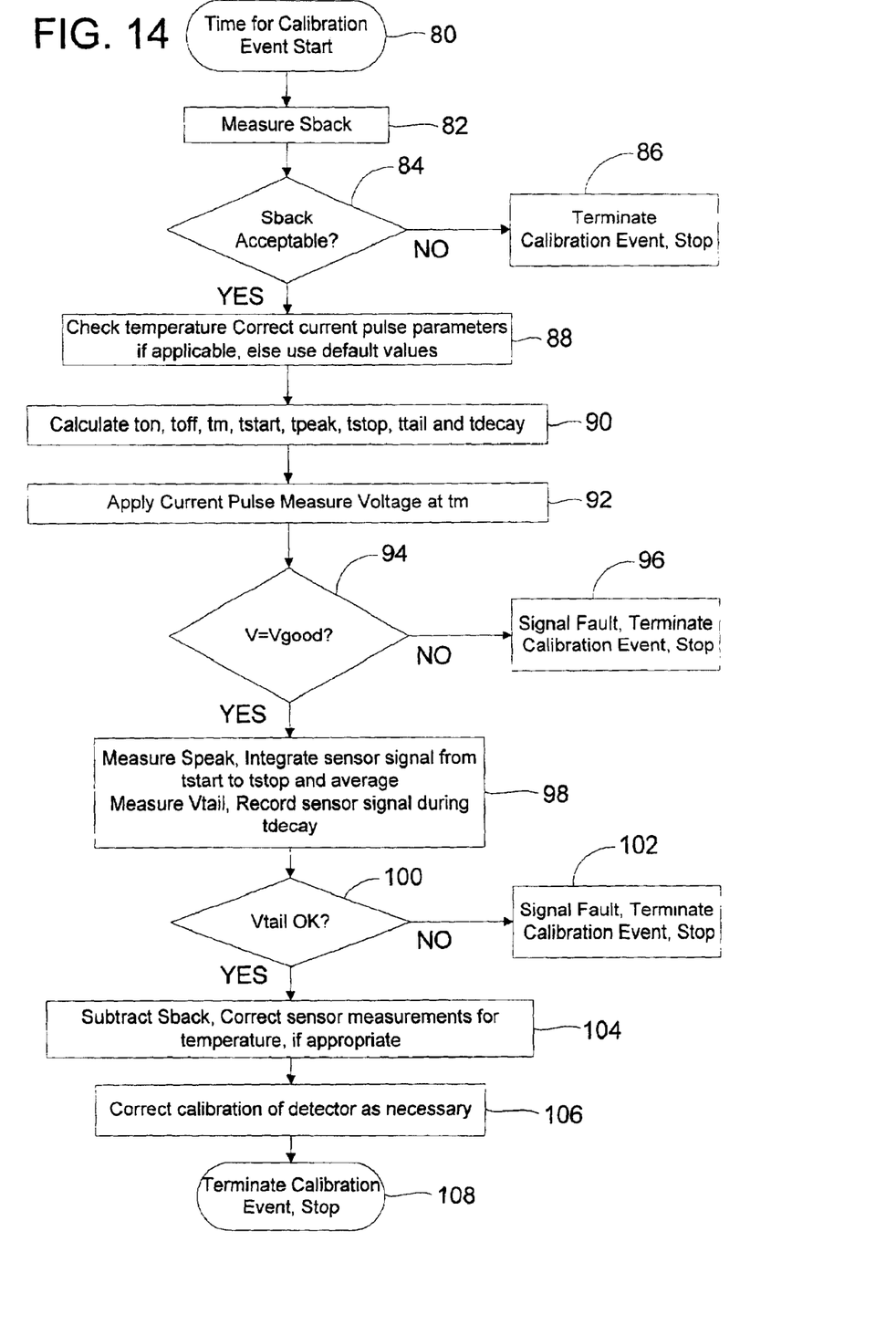
FIG. 14 is a simplified flow diagram illustrating a calibration method of the present invention.

The test/calibration method of the present invention is illustrated in simplified flow diagrammatic form in FIG. 14, to which specific reference is now made. Upon initiation of the test/calibration event 80, the system of the present invention measures 82 the background signal of the sensor 10 ($S_{back}$). If $S_{back}$ is too large, or if the value is not stable as determined by step 84, then the test/calibration event is terminated 86. The reason for this termination is discussed above in detail, and relates to the detector 44 possibly entering an alarm condition. However, if $S_{back}$ is not too large, or if the value is stable at step 84, the system of the present invention may continue with the test/calibration event.

In embodiments of the present invention that compensate the generator 12 for temperature variations, the temperature is checked and, if necessary, the current pulse control parameters are adjusted at step 88. If temperature compensation is required, the system then calculates the adjusted $t_{on}$, $t_{off}$, $t_{start}$, $t_{peak}$, $t_{stop}$, $t_{tail}$, and $t_{decay}$, at step 90. Alternatively, stored parametric may be used from a look-up table for different temperatures if such compensation is utilized.

To ensure that the generator 12 is operating properly, the current pulse is applied and the voltage across the generator 12 is measured at time $t_m$ at step 92. If the voltage is not within acceptable limits at step 94, a fault is signaled and the test/calibration event is terminated 96. However, if the voltage is within acceptable limits at step 94, the sensor parameters are measured at step 98, including measuring $S_{peak}$ and integrating the sensor signal from $t_{start}$ to $t_{stop}$ and averaging. The voltage $V_{tail}$ of the generator 12 is also measured, and preferably the sensor signal during $t_{decay}$ is also recorded. If the generator voltage $v_{tail}$ is not within acceptable limits at step 100, a fault is signaled and the test/calibration event is terminated at step 102.

If the generator 12 voltage $v_{tail}$ is acceptable at step 100, then the value of $S_{back}$ is subtracted at step 104 from the sensor signal (or average) as described above. Additionally, in embodiments of the present invention that utilize the temperature measurement to compensate the sensor reading to account for temperature variations of carbon monoxide production by the generator 12, the sensor measurements are corrected at this step 104. The calibration of the detector 44 is then corrected as necessary at step 106 to adjust for any variations in the sensor 10 as discussed above. Once this is accomplished, the test/calibration event is terminated at step 108.

All of the references cited herein, including patents, patent applications, and publications, are hereby incorporated in their entireties by reference.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A carbon monoxide detector, comprising:
    a housing forming a chamber therein, said housing including a first aperture;
    a carbon monoxide sensor assembly having a second aperture positioned within said chamber;
    a carbon monoxide gas generator assembly having a third aperture positioned within said chamber; and
    a controller coupled to said carbon monoxide sensor assembly and to said carbon monoxide gas generator assembly, said controller commanding said carbon monoxide gas generator assembly to produce carbon monoxide, said controller further monitoring an electrical output of said carbon monoxide sensor assembly to ensure proper operation thereof;
    said carbon monoxide gas generator assembly including:
    a can forming a water reservoir therein;
    a bottom disk positioned within said can to separate said water reservoir from an upper sensor portion of said can, said bottom disk including at least one aperture therein;
    a hydrophobic layer positioned on said bottom disk covering said at least one aperture;
    an electrode assembly positioned on said hydrophobic layer, said electrode assembly including an ion exchange membrane having electrodes deposited on an upper and on a lower surface thereof, said electrodes containing a mixture of carbon black and ion exchange polymer and no platinum;
    a diffusion layer;
    a gasket; and
    a top disk in sealing engagement with said gasket, said top disk defining an aperture therein; and
    wherein said can is crimped to seal said carbon monoxide gas generator assembly, said diffusion layer providing electrical contact between said top disk and a top of said electrode assembly, electrical contact between a bottom of said electrode assembly and said can being provided by said hydrophobic layer and said bottom disk.

2. The detector of claim 1, wherein said controller further monitors a voltage across said carbon monoxide gas generator assembly to ensure proper operation.

3. The detector of claim 2, wherein said controller signals a failure of said detector when said voltage across said carbon monoxide gas generator exceeds a predetermined level.

4. The detector of claim 2, wherein said controller signal a failure of said detector when said voltage across said carbon monoxide gas generator is below a first predetermined level and a decay of said voltage at a time $t_{tail}$ is above a second predetermined level.

5. The detector of claim 1, wherein said first aperture is diffusion limiting and said second and said third apertures are non-diffusion limiting.

6. The detector of claim 5, wherein each of said carbon monoxide sensor assembly and said carbon monoxide gas generator assembly includes a water reservoir.

7. The detector of claim 5, wherein said carbon monoxide sensor assembly includes a water reservoir.

8. The detector of claim 5, wherein said carbon monoxide sensor and said carbon monoxide gas generator assembly share said water reservoir.

9. The detector of claim 1, wherein said first aperture is non-diffusion limiting and said second and said third are diffusion limiting.

10. The detector of claim 9, wherein each of said carbon monoxide sensor assembly and said carbon monoxide gas generator assembly include a water reservoir.

11. The detector of claim 9, wherein both said carbon monoxide sensor assembly and said carbon monoxide gas generator assembly share a single water reservoir.

12. The detector of claim 1, wherein said first, said second, and said third apertures are in gaseous communication through said chamber.

13. The detector of claim 1, wherein said controller monitors said electrical output of said carbon monoxide sensor assembly prior to commanding said carbon monoxide gas generator assembly to produce carbon monoxide.

14. The detector of claim 13, wherein said controller inhibits said commanding of said carbon monoxide gas generator assembly to produce carbon monoxide when said electrical output of said carbon monoxide sensor assembly is greater than a predetermined level.

15. The detector of claim 13, wherein said controller monitors said electrical output of said carbon monoxide sensor assembly at a time $t_{peak}$ and during a period of signal decay, said controller further integrating said electrical output of said carbon monoxide sensor assembly from a time $t_{start}$ to a time $t_{stop}$, averaging over said time $t_{start}$ to a time $t_{stop}$ and subtracting said electrical output of said carbon monoxide sensor assembly monitored prior to commanding said carbon monoxide gas generator assembly to produce carbon monoxide to derive a measure of said carbon monoxide sensor assembly response.

16. The detector of claim 15, wherein said controller utilizes said measure of said carbon monoxide sensor assembly response to correct a calibration of said carbon monoxide sensor assembly.

17. The detector of claim 1, further comprising means for compensating for variations in an ambient temperature.

18. The detector of claim 17, wherein said means comprises ambient temperature sensing circuitry in communication with said controller.

19. The detector of claim 18, further comprising a programmed current source/sink controllably in communication with said controller and operatively in communication with said carbon monoxide gas generator assembly, said programmed current source/sink generating a current pulse having a magnitude and a duration, said current pulse being delivered to said carbon monoxide gas generator assembly under command of said controller to cause said carbon monoxide gas generator assembly to produce carbon monoxide, said controller commanding an adjustment in said magnitude of said current pulse as a function of said ambient temperature to produce a constant amount of carbon monoxide.

20. The detector of claim 18, further comprising a programmed current source/sink controllably in communication with said controller and operatively in communication with said carbon monoxide gas generator assembly, said programmed current source/sink generating a current pulse having a magnitude and a duration, said current pulse being delivered to said carbon monoxide gas generator assembly under command of said controller to cause said carbon monoxide gas generator assembly to produce carbon monoxide, said controller commanding an adjustment in said duration of said current pulse as a function of said ambient temperature to produce a constant amount of carbon monoxide.

21. The detector of claim 18, wherein said controller compensates said electrical output of said carbon monoxide sensor assembly as a function of said ambient temperature to account for a variation in an amount of carbon monoxide gas produced by said carbon monoxide gas generator assembly as a function of said ambient temperature.

22. The detector of claim 18, wherein said controller ensures that said ambient temperature is within a predetermined range prior to commanding said carbon monoxide gas generator to produce carbon monoxide.

23. The detector of claim 17, wherein said means comprise a temperature sensitive load resistor network coupled to said carbon monoxide sensor assembly to automatically compensate said electrical output of said carbon monoxide sensor assembly as a function of ambient temperature.

24. The detector of claim 17, wherein said means comprise a temperature sensitive amplifier coupled to said carbon monoxide sensor assembly to automatically compensate said electrical output of said carbon monoxide sensor assembly as a function of ambient temperature.

25. The detector of claim 1, wherein said carbon monoxide sensor assembly comprises:
a second can forming a second water reservoir therein;
a second bottom disk positioned within said second can to separate said second water reservoir from an upper sensor portion of said second can, said second bottom disk including an aperture therein;
a second hydrophobic layer positioned on said second bottom disk covering said aperture of said second bottom disk;
a second electrode assembly positioned on said second hydrophobic layer;
a first washer positioned on said second electrode assembly, said first washer having an outer periphery that is closely accommodated by an inner surface of said second can, said first washer further defining a hole therein having diameter that is smaller than a diameter of said second electrode assembly;
a second diffusion layer positioned on said first washer;
a second washer positioned on said second diffusion layer, said second washer having an outer periphery that is closely accommodated by said inner surface of said second can, said second washer further defining a hole therein having a diameter that is smaller than a diameter of said second diffusion layer;
a second gasket positioned on said second washer; and
a second top disk in sealing engagement with said second gasket, said second top disk defining an aperture therein; and
wherein said second can is crimped to seal said carbon monoxide sensor assembly, said second diffusion layer being deformed therein to provide electrical contact between said second top disk and a top of said second electrode assembly, electrical contact between a bottom of said second electrode assembly and said second can being provided by said second hydrophobic layer and said second bottom disk.

26. The detector of claim 25, wherein said second diffusion layer and said second hydrophobic layer comprises a microporous carbon loaded PTFE compound.

27. The detector of claim 25, wherein said second electrode assembly comprises an ion exchange membrane having an upper and a lower surface thereof coated with an electrode.

28. A carbon monoxide detector, comprising:
a housing forming a chamber therein, said housing including a first aperture;
a carbon monoxide sensor assembly having a second aperture positioned within said chamber;
a carbon monoxide gas generator assembly having a third aperture positioned within said chamber; and
a controller coupled to said carbon monoxide sensor assembly and to said carbon monoxide gas generator assembly, said controller commanding said carbon monoxide gas generator assembly to produce carbon monoxide, said controller further monitoring an electrical output of said carbon monoxide sensor assembly to ensure proper operation thereof;
wherein said carbon monoxide gas generator assembly including:
a can for a water reservoir therein;
a bottom disk positioned within said can to separate said water reservoir from an upper sensor portion of said can, said bottom disk including at least one aperture therein;
a hydrophobic layer positioned on said bottom disk covering said at least one aperture containing no platinum;
an electrode assembly positioned on said hydrophobic layer, said electrode assembly including an ion exchange membrane;
a diffusion layer containing no platinum positioned to contact said electrode assembly;
a gasket; and
a top disk in sealing engagement with said gasket, said top disk defining an aperture therein; and
wherein said can is crimped to seal said carbon monoxide gas generator assembly, said diffusion layer providing electrical contact between said top disk and a top of said electrode assembly, electrical contact between a bottom of said electrode assembly and said can being provided by said hydrophobic layer and said bottom disk and further comprising a first washer positioned on said electrode assembly, said first washer having an outer periphery that is closely accommodated by an inner surface of said can, said first washer further defining a hole therein having a diameter that is smaller than a diameter of said electrode assembly; and further comprising a second washer positioned on said diffusion layer, said second washer having an outer periphery that is closely accommodated by said inner surface of said can, said second washer further defining a hole therein having a diameter that is smaller than a diameter of said diffusion layer.

29. The detector of claim 1, further comprising a first washer positioned on said electrode assembly, said first washer having an outer periphery that is closely accommodated by an inner surface of said can, said first washer further defining a hole therein having a diameter that is smaller than a diameter of said electrode assembly.

30. The detector of claim 29, further comprising a second washer positioned on said diffusion layer, said second washer having an outer periphery that is closely accommodated by said inner surface of said can, said second washer further defining a hole therein having a diameter that is smaller than a diameter of said diffusion layer.

31. A carbon monoxide detector, comprising:

a housing forming a chamber therein, said housing including a first aperture;

a carbon monoxide sensor assembly having a second aperture positioned within said chamber;

a carbon monoxide gas generator assembly having a third aperture positioned within said chamber; and a controller coupled to said carbon monoxide sensor assembly and to said carbon monoxide gas generator assembly, said controller commanding said carbon monoxide gas generator assembly to produce carbon monoxide, said controller further monitoring an electrical output of said carbon monoxide sensor assembly to ensure proper operation thereof;

wherein said carbon monoxide gas generator assembly including:

a can forming a water reservoir therein;

a bottom disk positioned within said can to separate said water reservoir from an upper sensor portion of said can, said bottom disk including at least one aperture therein;

a hydrophobic layer positioned on said bottom disk covering said at least one aperture containing no platinum;

an electrode assembly positioned on said hydrophobic layer, said electrode assembly including an ion exchange membrane;

a diffusion layer containing no platinum positioned to contact said electrode assembly;

a gasket; and a top disk in sealing engagement with said gasket, said top disk defining an aperture therein; and wherein said can is crimped to seal said carbon monoxide gas generator assembly, said diffusion layer providing electrical contact between said top disk and a top of said electrode assembly, electrical contact between a bottom of said electrode assembly and said can being provided by said hydrophobic layer and said bottom disk.

32. A carbon monoxide detector, comprising:

a housing forming a chamber therein, said housing including a first aperture;

a carbon monoxide sensor assembly having a second aperture positioned within said chamber;

a carbon monoxide gas generator assembly having a third aperture positioned within said chamber; and a controller coupled to said carbon monoxide sensor assembly and to said carbon monoxide gas generator assembly, said controller commanding said carbon monoxide gas generator assembly to produce carbon monoxide, said controller further monitoring an electrical output of said carbon monoxide sensor assembly to ensure proper operation thereof;

where said carbon monoxide gas generator assembly including:

a can forming a water reservoir therein;

a bottom disk positioned within said can to separate said water reservoir from an upper sensor portion of said can, said bottom disk including at least one aperture therein;

a hydrophobic layer positioned on said bottom disk covering said at least one aperture containing no platinum;

an electrode assembly positioned on said hydrophobic layer, said electrode assembly including an ion exchange membrane;

a diffusion layer containing no platinum positioned to contact said electrode assembly;

a gasket; and a top disk in sealing engagement with said gasket, said top disk defining an aperture therein; and wherein said can is crimped to seal said carbon monoxide gas generator assembly, said diffusion layer providing electrical contact between said top disk and a top of said electrode assembly, electrical contact between a bottom of said electrode assembly and said can being provided by said hydrophobic layer and said bottom disk; and further comprising a first washer positioned on said electrode assembly, said first washer having an outer periphery that is closely accommodated by an inner surface of said can, said first washer further defining a hole therein having a diameter that is smaller than a diameter of said electrode assembly.

* * * * *